US012698145B2

(12) United States Patent
Nalawade et al.

(10) Patent No.: US 12,698,145 B2
(45) Date of Patent: Aug. 4, 2026

(54) FLUID DISPENSING DEVICE

(71) Applicant: Becton, Dickinson and Company,
Franklin Lakes, NJ (US)

(72) Inventors: Praveen Nalawade, Bangaluru (IN);
Shishir Prasad, Ramsey, NJ (US)

(73) Assignee: Becton, Dickinson and Company,
Franklin Lakes, NJ (US)

( * ) Notice: Subject to any disclaimer, the term of this
patent is extended or adjusted under 35
U.S.C. 154(b) by 130 days.

(21) Appl. No.: 18/473,477

(22) Filed: Sep. 25, 2023

(65) Prior Publication Data

US 2025/0100777 A1     Mar. 27, 2025

(51) Int. Cl.
| | |
|---|---|
| *B65D 83/00* | (2006.01) |
| *A61M 5/24* | (2006.01) |
| *B65D 41/28* | (2006.01) |
| *B65D 47/14* | (2006.01) |
| *B65D 55/16* | (2006.01) |

(52) U.S. Cl.
CPC ....... *B65D 83/0094* (2013.01); *A61M 5/2425*
(2013.01); *B65D 41/28* (2013.01); *B65D*
*47/141* (2013.01); *B65D 55/16* (2013.01)

(58) Field of Classification Search
CPC .......................... A61M 5/2425; B65D 83/0094
See application file for complete search history.

(56) References Cited

U.S. PATENT DOCUMENTS

| | | | | |
|---|---|---|---|---|
| 3,938,514 | A | * | 2/1976 | Boucher ............. A61M 3/0262 |
| | | | | 222/206 |
| 4,753,638 | A | * | 6/1988 | Peters .............. A61B 5/150343 |
| | | | | 604/212 |
| 5,242,422 | A | * | 9/1993 | Schneberger ....... A61M 5/3137 |
| | | | | 222/206 |
| 5,333,761 | A | * | 8/1994 | Davis ................... B65D 1/0292 |
| | | | | 222/215 |
| 5,385,372 | A | * | 1/1995 | Utterberg .............. A61M 39/20 |
| | | | | 285/391 |
| 5,836,922 | A | * | 11/1998 | Hansen ................. A61M 5/282 |
| | | | | 222/541.2 |
| 6,319,235 | B1 | * | 11/2001 | Yoshino ........... A61B 5/150519 |
| | | | | 604/212 |
| 6,332,876 | B1 | * | 12/2001 | Poynter ................. A61M 5/282 |
| | | | | 604/212 |

(Continued)

FOREIGN PATENT DOCUMENTS

| | | | |
|---|---|---|---|
| DE | 202012100925 U1 | 4/2012 | |
| WO | 2013158425 A1 | 10/2013 | |

*Primary Examiner* — Timothy L Maust
(74) *Attorney, Agent, or Firm* — The Webb Law Firm

(57) ABSTRACT

A fluid delivery device, such as a syringe, is disclosed,
including a bellows structure defining a first end, a second
end, and a cavity therein, where compressing the bellows
structure reduces a height of the syringe; a tip adjacent the
first end, the tip defining a channel in fluid communication
with the cavity; a post coaxial with the channel and disposed
in the cavity adjacent the second end of the bellows struc-
ture; a laterally-extending flange adjacent the first end of the
bellows structure, the flange defining a width greater than a
width of the bellows structure; an adaptor adjacent the tip,
the adaptor defining a wall and a threaded interface on an
interior surface thereof; and a cap releasably engageable
with the tip.

11 Claims, 8 Drawing Sheets

(56)             References Cited

U.S. PATENT DOCUMENTS

| | | | | |
|---|---|---|---|---|
| 6,866,039 | B1 * | 3/2005 | Wright .............. | A61M 15/0028 |
| | | | | 222/321.6 |
| 9,180,252 | B2 | 11/2015 | Gelblum et al. | |
| 9,737,664 | B2 * | 8/2017 | Gardner .............. | A61M 5/2425 |
| 10,543,317 | B2 * | 1/2020 | Basile ................. | A61M 5/3137 |
| 2006/0287639 | A1 * | 12/2006 | Sharp ................... | A61J 1/2096 |
| | | | | 604/415 |
| 2010/0095957 | A1 * | 4/2010 | Corbacho ......... | A61M 15/0028 |
| | | | | 128/200.14 |
| 2013/0118484 | A1 | 5/2013 | Ishikita | |
| 2016/0058946 | A1 | 3/2016 | Gelblum et al. | |
| 2019/0234540 | A1 | 8/2019 | Marici et al. | |
| 2020/0376201 | A1 | 12/2020 | Gardner et al. | |
| 2021/0244888 | A1 * | 8/2021 | Ryan ..................... | A61M 5/347 |
| 2021/0353867 | A1 | 11/2021 | Mahmoodian | |
| 2022/0184368 | A1 | 6/2022 | Lopez et al. | |

* cited by examiner

FLUID DISPENSING DEVICE

FIELD OF THE INVENTION

The present disclosure relates to devices and methods of use thereof for storing, transporting, and dispensing fluids.

BACKGROUND OF THE INVENTION

Conventional plunger-operated syringes are used extensively in medical, industrial, and other industries to controllably deliver or dispense fluid. Such devices typically include a barrel containing a liquid, a plunger movable in the barrel to introduce or disperse fluid from the barrel, and a stopper to limit movement of the plunger within the barrel. Despite ubiquitous use and seemingly simplistic operation, these syringes can nevertheless introduce failures or complications in the filling, storage, transport, and use thereof. For example, one or more components may insufficiently form a seal, leading to leakage of the fluid contents. The components of the syringe and/or a lubricant used therein may compromise or introduce contaminants into a fluid contained in the barrel. A pre-filled syringe may have larger packaging and storage requirements to accommodate a length of an extended plunger, which also increases the amount of waste generated once the syringe has been used. The present disclosure provides devices and methods of use thereof that overcome such drawbacks.

SUMMARY OF THE INVENTION

The present disclosure provide a device for dispensing fluid, including a bellows structure defining a first end, a second end, and a cavity therein, wherein compressing the bellows structure reduces a height of the device; a tip adjacent the first end, the tip defining a channel in fluid communication with the cavity; and a flange adjacent the first end, the flange defining a width greater than a width of the bellows structure. The flange may include one or more tactile elements. The device may include a post disposed in the cavity adjacent the second end of the bellows structure, where the post is optionally at least partially disposed within the channel of the tip when the bellows structure is compressed. The device may include a base adjacent the second end of the bellows structure, the base having a width greater than the width of the bellows structure. The base may include a plurality of tactile elements thereon. The device may include a cap releasably engageable with the tip. The cap may include a protrusion positionable within the channel of the tip and/or may be attached to the flange by a living hinge. The device may include a threaded interface adjacent the tip. The threaded interface may include a wall circumscribing the tip, with the wall defining a plurality of threads on an interior surface thereof. The device may include a cap releasably engageable with the threaded interface.

A syringe is disclosed, including a bellows structure defining a first end, a second end, and a cavity therein, wherein compressing the bellows structure reduces a height of the syringe; a tip adjacent the first end, the tip defining a channel in fluid communication with the cavity; a threaded interface adjacent the tip; and a post disposed in the cavity adjacent the second end of the bellows structure. The syringe may include a depressible surface extending laterally from the bellows structure, where the depressible surface is positioned adjacent to the first end of the bellows structure. The depressible surface may define a width greater than a width of the bellows structure. The post may be at least partially disposed within the channel of the tip when the bellows structure is compressed. The syringe may include a cap releasably engageable with the tip. The threaded interface may include a wall circumscribing the tip, with the wall defining a plurality of threads on an interior surface thereof.

A syringe is disclosed, including a bellows structure defining a first end, a second end, and a cavity therein, wherein compressing the bellows structure reduces a height of the syringe; a tip adjacent the first end, the tip defining a channel in fluid communication with the cavity; a post coaxial with the channel and disposed in the cavity adjacent the second end of the bellows structure; a laterally-extending flange adjacent the first end of the bellows structure, the flange defining a width greater than a width of the bellows structure; an adaptor adjacent the tip, the adaptor defining a wall and a threaded interface on an interior surface thereof; and a cap releasably engageable with the tip.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE INVENTION

Figure 1:
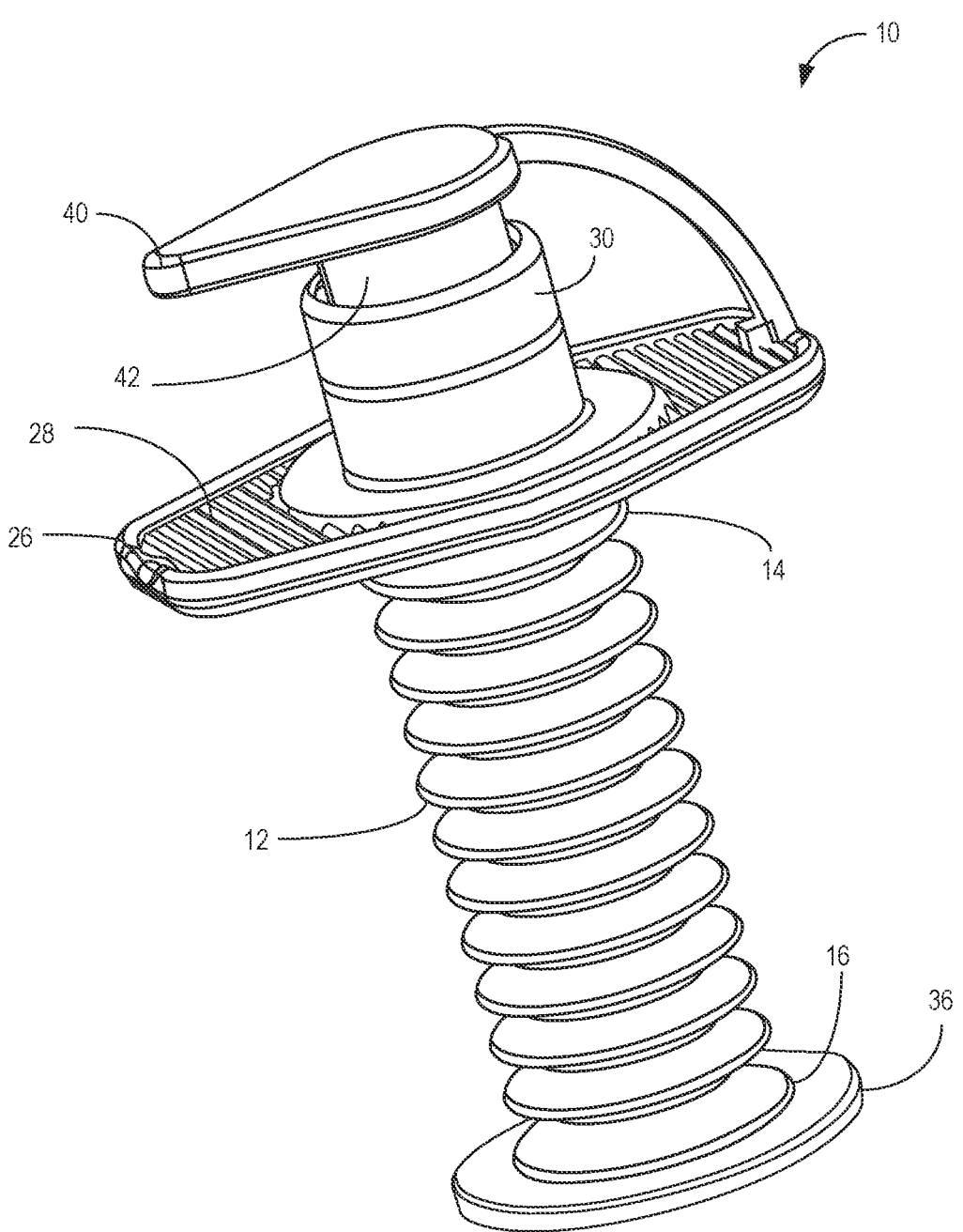
FIG. 1 is an isometric view of an example of a device for dispensing fluid constructed in accordance with the principles of the present disclosure.
Figure 2:
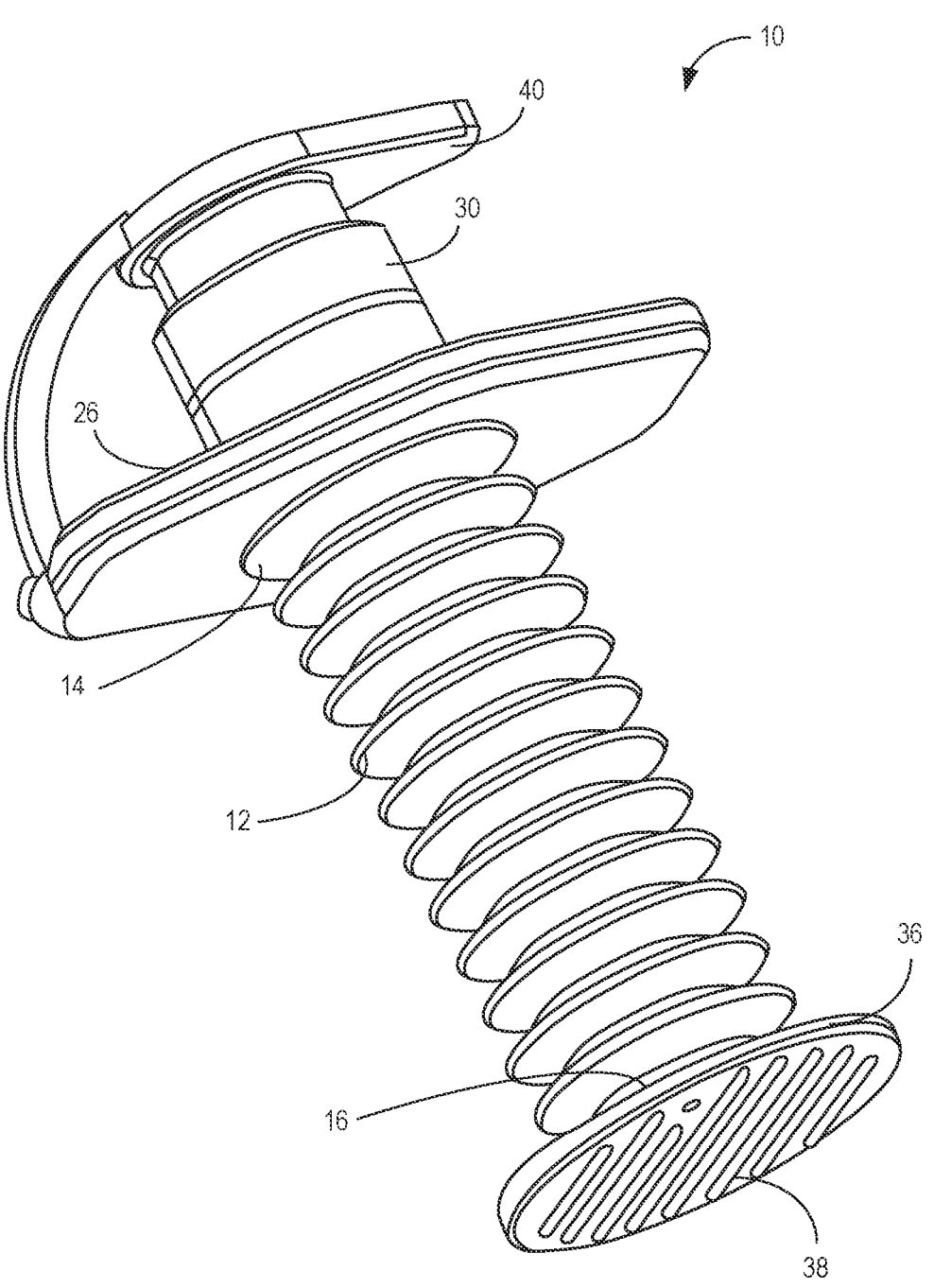
FIG. 2 is another isometric view of the device for dispensing fluid shown in FIG. 1.
Figure 3:
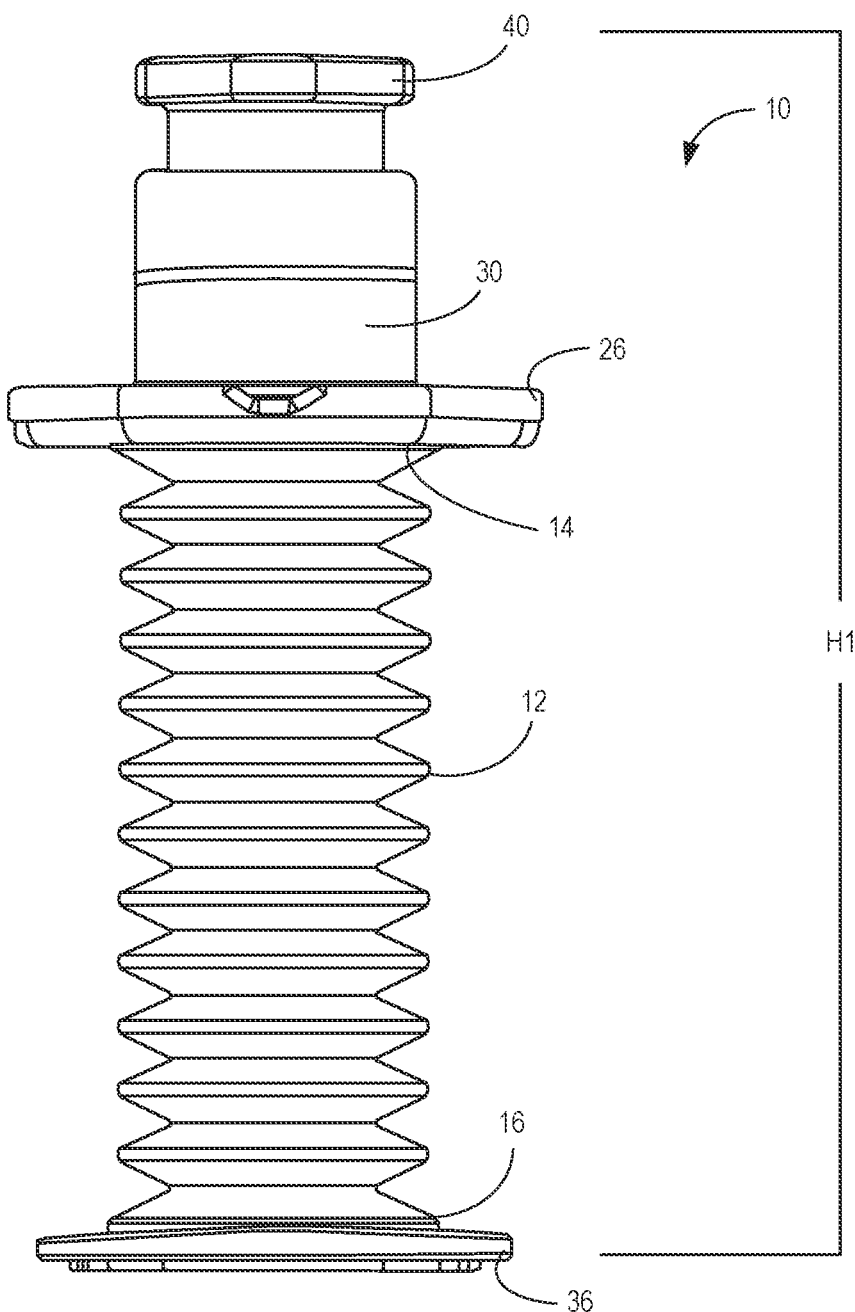
FIG. 3 is a first side view of the device for dispensing fluid shown in FIG. 1.
Figure 4:
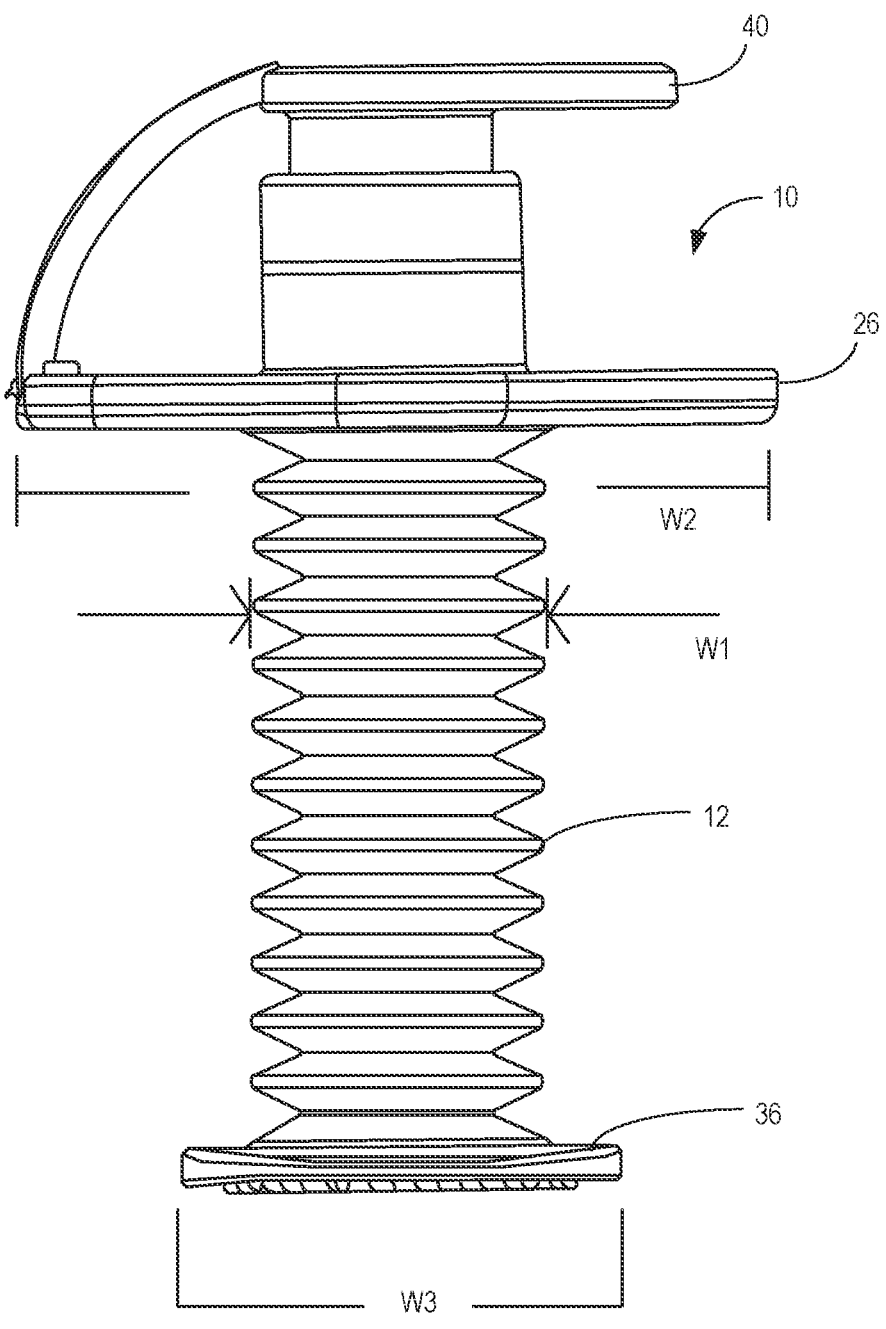
FIG. 4 is a second side view of the device for dispensing fluid shown in FIG. 1.

The present disclosure provides devices and methods of use thereof for dispensing fluids. Such fluids may include biological, pharmaceutical, or other therapeutic or medical compounds used in a treatment environment, and/or may include industrial or other commercial compounds as applicable. Referring now to the drawing figures in which like reference designations refer to like elements, examples of a device 10 for dispensing a fluid are shown in FIGS. 1-8.

The device 10 may generally, for example, be a syringe, injector, dispenser or other instrument operable to controllably deliver a fluid or compound. The device may include or define a bellows structure 12 extending along a length thereof. The bellows structure 12 may include or define an accordion-like structure with a plurality of pleated or folded segments operable to expand and compress. The bellows structure may form a first end or distal end 14, a second end or proximal end 16, and a cavity 18 therein disposed between the first and second ends. The device 10 may define an overall height H1 and a width W1, and the bellows structure 12 may be integrated into or otherwise form a portion of the device 10 such that expansion and compression of the bellows structure 12 changes the height H1 of the device, as comparatively illustrated in FIGS. 5 and 6. The volumetric capacity and the compressibility of the bellows structure 12 may be modified or selected at least in part by the quantity of folded segments of the bellows structure 12, as well as by the rigidity or thickness of the material constituting the bellows structure 12. In one example, each folded segment could be compressed to directly contact each other along the diameter of the bellows structure to minimize space therein when compressed.

The device 10 may include a tip or nozzle 20 attached and/or adjacent to the first end 14 of the bellows structure 12. The tip 20 may define or include a channel 22 therein that is in fluid communication with the cavity 18 and thus operable to transfer fluid into and out of the cavity 18.

The device 10 may include a post 24 disposed in the cavity 18. The post 24 may be sized and shaped to reduce the volumetric capacity or 'dead space' within the bellows structure 12 when compressed to reduce the amount of fluid remaining in the cavity 18 in the compressed state. The post 20 may be positioned and/or attached adjacent to the second end 16 of the bellows structure 12, and may have a conical, frustoconical, rectangular, cylindrical, or other geometric profile.

The post 24 may be coaxially aligned with the tip 20 and/or channel 22, and the post 24 may define a height H2 of sufficient dimension such that at least a portion of the post 24 is disposed within or adjacent to the channel 22 of the tip 20 when the bellows structure 12 is in a compressed state.

The device 10 may include or define a depressible surface 26 attached to or integrated thereon to enable or facilitate manual operation of the device 10. For example, the depressible surface 26 may include one or more flanges, rims, wings, protrusions, finger loops, or the like that provide an area or surface for a user's fingers to grasp during compression of the bellows structure 12 as described herein. The depressible surface 26 may define a width W2 greater than width W1 of the bellows structure 12 (as used herein, the widths W1, W2, etc. are comparative lateral width measurements in a single plane, such as that shown in FIG. 4). The depressible surface may be attached to or otherwise located adjacent to the first end 14 of the bellows structure 12, or alternatively may be disposed at one or more other locations along the height of the device 10. One or more tactile elements 28 may be positioned on or integrated with the depressible surface 26 to enhance or improve a user's grip on the device 10. For example, the tactile element(s) 28 may include one or more ridges, ribs, indentations, or protrusions to reduce the likelihood of slippage during use.

The device 10 may include one or more features rendering the device 10 engageable with another device, instrument, or the like for the receipt or delivery of fluids. For example, the device 10 may include an adaptor 30 attached to or integrated into the device 10 adjacent to the tip 20. The adaptor 30 may include or define a wall 32 circumscribing or otherwise in proximity to the tip 20, with one or more threaded interfaces 34 thereon. In the illustrated example, the threaded interface 34 is on an interior surface of the wall 32, however, alternative examples may include exterior threading, one or more compression fit features, or other releasably engageable interconnections.

The device 10 may include or define a base 36 attached to or integrated with the bellows structure 12 at or adjacent to the second end 16 of the bellows structure 12. The base 36 may include or define a surface facilitating the manual compression or expansion of the bellows structure 12, and/or provide a surface of sufficient dimension to stack or store one or more of the devices 10 in an upright position. The base 36 may define a width W3 greater than the width W1 of the bellows structure. The base 36 may also include one or more tactile elements 38 positioned on or integrated therewith to enhance or improve a user's grip on the device 10. For example, the tactile element(s) 38 may include one or more ridges, ribs, indentations, or protrusions to reduce the likelihood of slippage during use.

Figure 5:
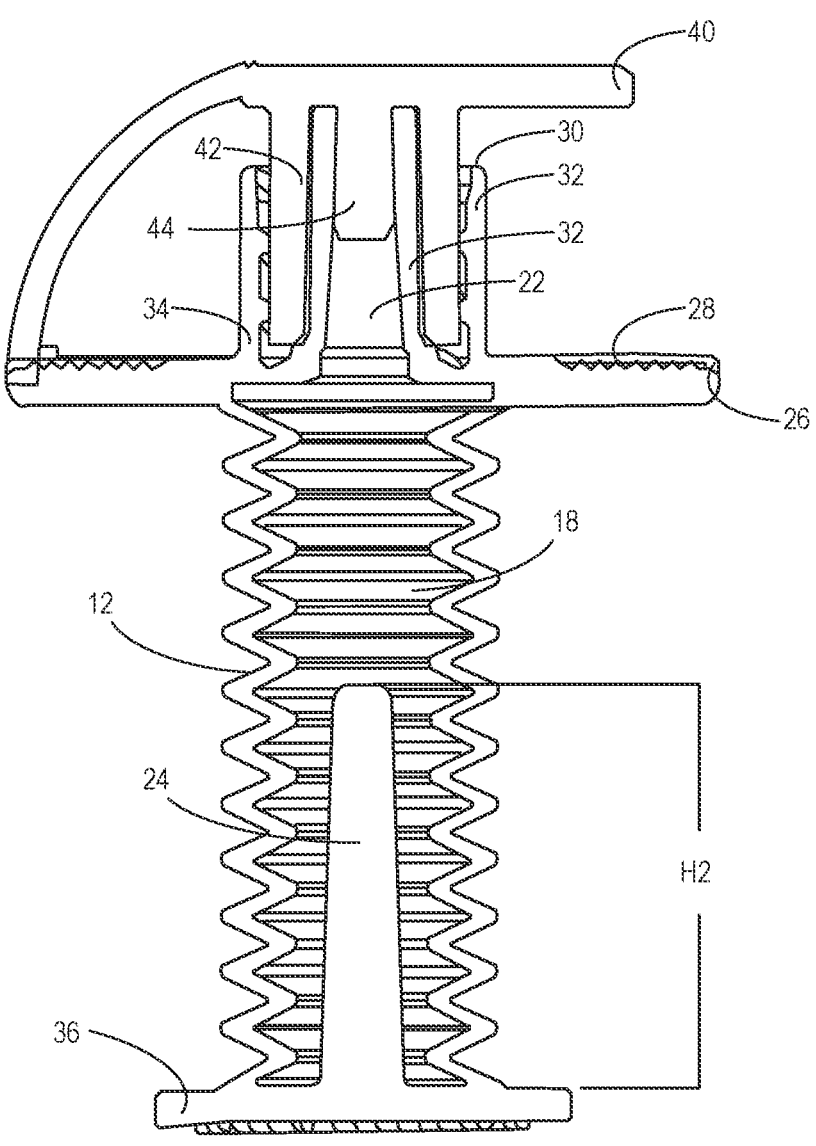
FIG. 5 is a cross-sectional view of the device for dispensing fluid shown in FIG. 1 while in an expanded state.
Figure 6:
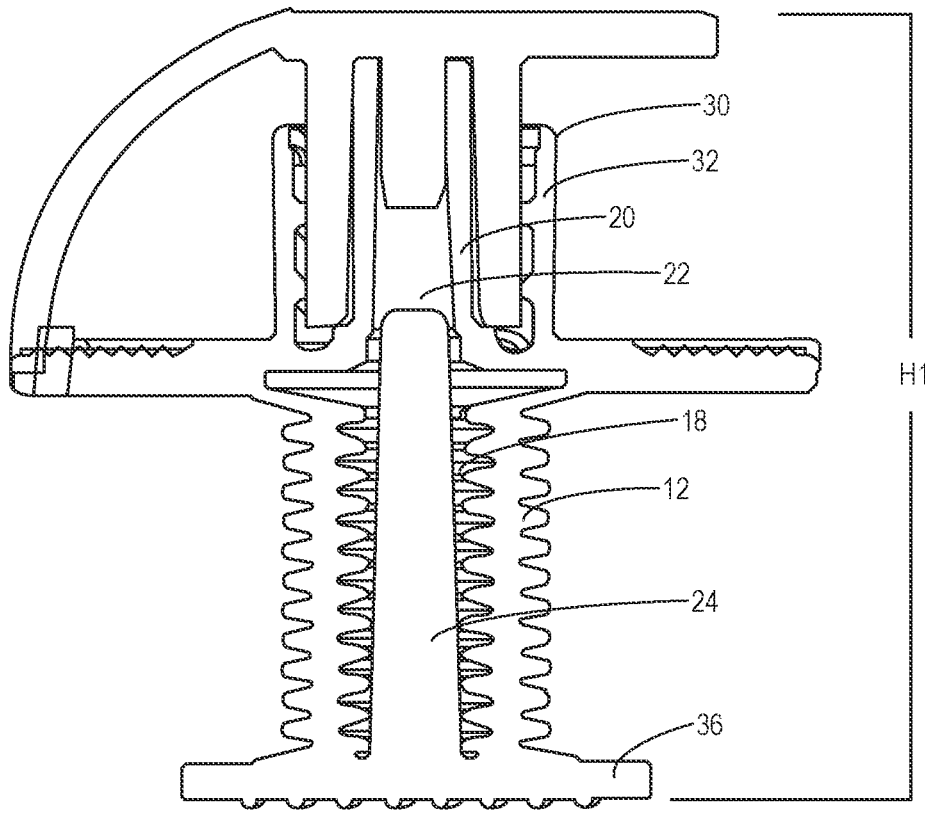
FIG. 6 is a cross-sectional view of the device for dispensing fluid shown in FIG. 1 while in a compressed state.
Figure 7:
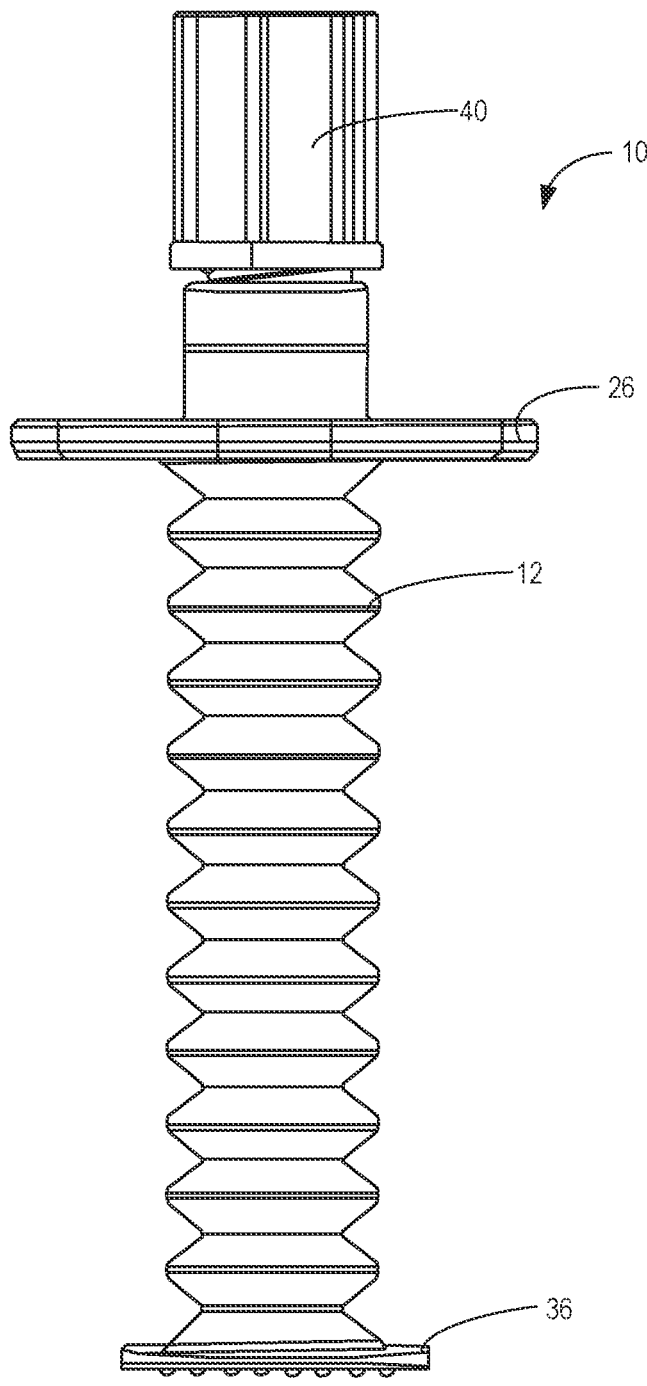
FIG. 7 is a first side view of another example of a device for dispensing fluid constructed in accordance with the principles of the present disclosure.
Figure 8:
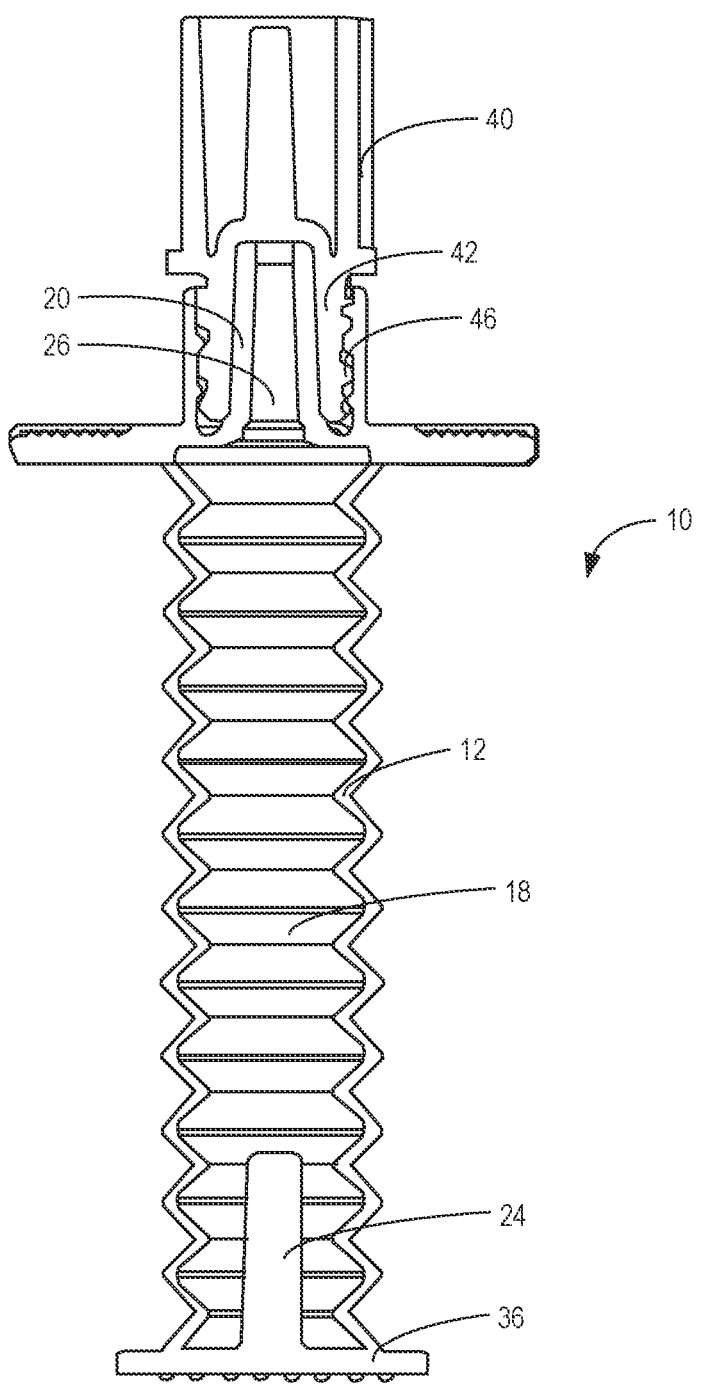
FIG. 8 is a second side view of the device for dispensing fluid shown in FIG. 7.

The device 10 may include a cap 40 releasably engageable with the tip 20 and/or channel 22 to either prevent or allow fluid to pass therethrough. The cap 40 may be attached to the device 10 through a living hinge or other tethering mechanism. In the illustrated example, the cap 40 is connected to the depressible surface 26. The cap 40 may define or include features matable with the tip 20, channel, 22, and/or the adaptor 30. For example, the cap 40 may define a wall 42 positionable between the wall 32 of the adaptor 30 and an exterior surface of the tip 20, and/or may include a protrusion 44 positionable within the channel 22 to substantially seal the channel 22 and thus the cavity 18. The cap 40 may form a compression fit with the tip 20 and/or adaptor 30, as shown in FIGS. 5 and 6, or may alternatively have a threaded surface 46 to engage the threaded interface 34 of the adaptor 30 to close or seal the device 10, as shown in FIGS. 7 and 8.

In an exemplary method of use, the device 10 may first be pre-filled with a fluid for later delivery. For example, the device 10 may be manufactured and provided in a state where the bellows structure 12 is compressed. A fluid may then be introduced into the channel 22 of the tip 20, upon which an axial force may be applied to the base 36 or other portion of the device 10 to expand the bellows structure 12 for continued filling. Once the desired fill level of fluid in the cavity 18 has been achieved, the cap 40 may be used to seal the tip 20 and/or channel 22. The device may then be stored, transported, or otherwise secured until use. Use of the device 10 may include removing the cap 40, and engaging the base 36 and/or depressible surface 26 to compress the bellows structure 12, thus moving the fluid from the cavity 18 into the channel 22 and out of the device 10. The dispersal of fluid may be through a needle hub, delivery line, or other fluid conduit (not shown) coupled to the device 10 by the adaptor 30.

The devices, features, and methods of sue thereof provide a myriad of attendant advantages over conventional fluid delivery devices, and in particular, plunger barrel syringes, including avoiding leaks due to compromised or ill-fitting seals between a plunger and a syringe barrel and avoidance of contaminating a fluid contents with lubricants or other chemical components of a plunger, stopper, or barrel. The devices disclosed herein further reduce packaging and storage sizing by avoiding a need to accommodate an elongated plunger length extending from a pre-filled barrel, and also reduce the waste generated by the device after use.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. A device for dispensing fluid, comprising:
a bellows structure defining a first end, a second end, and a cavity therein, wherein compressing the bellows structure reduces a height of the device;
a tip adjacent the first end, the tip defining a channel in fluid communication with the cavity;
a flange adjacent the first end, the flange defining a width greater than a width of the bellows structure;
a threaded interface adjacent the tip, the threaded interface including a wall circumscribing the tip, the wall defining a plurality of threads on an interior surface thereof; and
a cap releasably engageable with the tip, the cap defining a protrusion positionable within the channel of the tip and a cap wall having a cylindrical exterior surface releasably engageable with the threaded interface,
wherein the cap is attached to the flange by a living hinge at an outer edge portion of the flange, and
wherein when the protrusion is positioned within the channel of the tip, the cylindrical exterior surface of the cap wall contacts the threads to engage the threaded interface and seal the tip.

2. The device of claim 1, wherein the flange includes one or more tactile elements.

3. The device of claim 1, further comprising a post disposed in the cavity adjacent the second end of the bellows structure.

4. The device of claim 3, wherein the post is at least partially disposed within the channel of the tip when the bellows structure is compressed.

5. The device of claim 1, further comprising a base adjacent the second end of the bellows structure, the base having a width greater than the width of the bellows structure.

6. The device of claim 5, wherein the base includes a plurality of tactile elements thereon.

7. A syringe, comprising:
a bellows structure defining a first end, a second end, and a cavity therein, wherein compressing the bellows structure reduces a height of the syringe;
a tip adjacent the first end, the tip defining a channel in fluid communication with the cavity;

a threaded interface adjacent the tip, the threaded interface including a wall circumscribing the tip, the wall defining a plurality of threads on an interior surface thereof;
a post disposed in the cavity adjacent the second end of the bellows structure;
a depressible surface extending laterally from the bellows structure; and
a cap releasably engageable with the tip, the cap defining a protrusion positionable within the channel of the tip and a cap wall having a cylindrical exterior surface releasably engageable with the threaded interface,
wherein the cap is attached to the depressible surface by a living hinge at an outer edge portion of the depressible surface, and
wherein when the protrusion is positioned within the channel of the tip, the cylindrical exterior surface of the cap wall contacts the threads to engage the threaded interface and seal the tip.

8. The syringe of claim 7, wherein the depressible surface is positioned adjacent to the first end of the bellows structure.

9. The syringe of claim 7, wherein the depressible surface defines a width greater than a width of the bellows structure.

10. The syringe of claim 7, wherein the post is at least partially disposed within the channel of the tip when the bellows structure is compressed.

11. A syringe, comprising:
a bellows structure defining a first end, a second end, and a cavity therein, wherein compressing the bellows structure reduces a height of the syringe;
a tip adjacent the first end, the tip defining a channel in fluid communication with the cavity;
a post coaxial with the channel and disposed in the cavity adjacent the second end of the bellows structure;
a laterally-extending flange adjacent the first end of the bellows structure, the flange defining a width greater than a width of the bellows structure;
an adaptor adjacent the tip, the adaptor defining a threaded interface, the threaded interface including a wall circumscribing the tip, the wall defining a plurality of threads on an interior surface thereof; and
a cap releasably engageable with the tip, the cap defining a protrusion positionable within the channel of the tip and a cap wall having a cylindrical exterior surface releasably engageable with the threaded interface,
wherein the cap is attached to the flange by a living hinge at an outer edge portion of the flange, and
wherein when the protrusion is positioned within the channel of the tip, the cylindrical exterior surface of the cap wall contacts the threads to engage the threaded interface and seal the tip.

* * * * *